(12) United States Patent
Tucker et al.

(10) Patent No.: US 10,092,250 B2
(45) Date of Patent: Oct. 9, 2018

(54) CONTROL UNIT FOR A MEDICAL DEVICE

(75) Inventors: Carl Estcourt Tucker, Old Colwyn (GB); Troy A. Baker, St. Asaph (GB); Graham Peter Wilson, Flint (GB); Patrick Gerrard Linnane, Little Sutton (GB); Ian Stewart Tabron, Cheshire (GB); Wayne Lee Bonnefin, Chester (GB); Stefan Loof, Arsta (SE); Thomas Bergens, Ingaro (SE)

(73) Assignee: SWELLING SOLUTIONS, INC., Minneapolis, MN (US)

( * ) Notice: Subject to any disclaimer, the term of this patent is extended or adjusted under 35 U.S.C. 154(b) by 1443 days.

(21) Appl. No.: 11/626,043

(22) Filed: Jan. 23, 2007

(65) Prior Publication Data
US 2007/0249976 A1    Oct. 25, 2007

(30) Foreign Application Priority Data
Jan. 24, 2006    (GB) .................................. 0601451.8

(51) Int. Cl.
*A61H 9/00* (2006.01)
*A61B 5/00* (2006.01)

(52) U.S. Cl.
CPC ......... *A61B 5/7475* (2013.01); *A61H 9/0078* (2013.01); *A61B 2560/0456* (2013.01); *A61H 2201/0134* (2013.01); *A61H 2201/0146* (2013.01); *A61H 2201/5002* (2013.01); *A61H 2201/5007* (2013.01); *A61H 2205/10* (2013.01); *A61H 2205/12* (2013.01)

(58) Field of Classification Search
CPC .......... A61B 2560/0456; A61H 9/0078; A61H 9/0092

USPC .......................... 601/148, 149, 150, 151, 152
See application file for complete search history.

(56) References Cited

U.S. PATENT DOCUMENTS

| 5,022,387 | A | | 6/1991 | Hasty |
|---|---|---|---|---|
| 5,117,812 | A | | 6/1992 | McWhorter |
| 5,263,473 | A | | 11/1993 | McWhorter |
| 5,383,894 | A | | 1/1995 | Dye |
| 5,575,762 | A | | 11/1996 | Peeler et al. |
| 5,626,556 | A | | 5/1997 | Tobler et al. |
| 5,687,732 | A | | 11/1997 | Inagaki et al. |
| 5,795,312 | A | * | 8/1998 | Dye .............................. 601/151 |
| 5,843,007 | A | | 12/1998 | McEwen et al. |
| 5,876,359 | A | | 3/1999 | Bock et al. |

(Continued)

FOREIGN PATENT DOCUMENTS

| EP | 0329470 | 8/1989 |
|---|---|---|
| EP | 1018329 B1 | 7/2000 |

(Continued)

OTHER PUBLICATIONS

Grayline Inc Polyurethane Tubing http://www.graylineinc.com/tubing-materials/polyurethane.html.*

(Continued)

*Primary Examiner* — LaToya M Louis
(74) *Attorney, Agent, or Firm* — Mueting, Raasch & Gebhardt, P.A.

(57) ABSTRACT

A control unit for a medical device wherein the control unit includes a pump, a conduit and control means for controlling the flow of fluid from the pump through the conduit; and wherein the conduit is a rigid internal passage located in the control unit.

20 Claims, 3 Drawing Sheets

(56) References Cited

U.S. PATENT DOCUMENTS

| | | |
|---|---|---|
| 5,951,502 A | 9/1999 | Peeler et al. |
| 6,007,559 A | 12/1999 | Arkans |
| 6,041,243 A * | 3/2000 | Davidson et al. ......... 455/575.1 |
| 6,062,244 A | 5/2000 | Arkans |
| 6,123,681 A | 9/2000 | Brown |
| 6,198,204 B1 | 3/2001 | Pottenger |
| 6,231,532 B1 | 5/2001 | Watson |
| 6,290,662 B1 * | 9/2001 | Morris et al. ................ 601/149 |
| 6,296,617 B1 | 10/2001 | Peeler et al. |
| 6,355,008 B1 | 3/2002 | Nakao |
| 6,440,093 B1 | 8/2002 | McEwen et al. |
| 6,463,934 B1 | 10/2002 | Johnson, Jr. et al. |
| 6,544,202 B2 | 4/2003 | McEwen et al. |
| 6,558,338 B1 | 5/2003 | Wasserman |
| 6,620,116 B2 | 9/2003 | Lewis |
| 6,749,556 B2 | 6/2004 | Banik |
| 6,846,295 B1 | 1/2005 | Ben-Nun |
| 6,960,159 B2 * | 11/2005 | Chung et al. ................... 600/15 |
| 6,988,423 B2 | 1/2006 | Bolam et al. |
| 7,001,384 B2 | 2/2006 | Berish et al. |
| 7,056,297 B2 | 6/2006 | Dohno et al. |
| 7,074,200 B1 | 7/2006 | Lewis |
| 7,354,410 B2 | 4/2008 | Perry et al. |
| 7,442,175 B2 | 10/2008 | Meyer et al. |
| 7,491,185 B2 | 2/2009 | Couvillon, Jr. |
| 7,618,384 B2 | 11/2009 | Nardi et al. |
| 7,637,879 B2 | 12/2009 | Barak et al. |
| 7,637,922 B2 | 12/2009 | Johnson et al. |
| 7,868,221 B2 | 1/2011 | Munch-Fals et al. |
| 7,992,217 B2 | 8/2011 | Hyde et al. |
| 8,029,451 B2 | 10/2011 | Meyer et al. |
| 8,079,969 B2 | 12/2011 | Rousso et al. |
| 8,079,970 B2 | 12/2011 | Meyer et al. |
| 8,100,842 B2 | 1/2012 | Rousso |
| 8,105,252 B2 | 1/2012 | Rousso |
| 8,100,841 B2 | 12/2012 | Rousso |
| 2001/0002840 A1 * | 6/2001 | Casserino et al. ............. 347/85 |
| 2002/0091344 A1 * | 7/2002 | Thomas et al. ............... 601/148 |
| 2004/0073146 A1 | 4/2004 | Weintraub et al. |
| 2005/0159690 A1 * | 7/2005 | Barak et al. .................. 601/149 |
| 2005/0187503 A1 * | 8/2005 | Tordella et al. ................ 602/13 |
| 2006/0074362 A1 | 4/2006 | Rousso et al. |
| 2006/0111655 A1 * | 5/2006 | Cook et al. .................... 601/151 |
| 2006/0258964 A1 * | 11/2006 | Biondo et al. ................. 601/152 |
| 2006/0287672 A1 | 12/2006 | McEwen et al. |
| 2008/0039752 A1 * | 2/2008 | Rousso .......................... 601/134 |
| 2008/0188782 A1 * | 8/2008 | Carkner et al. ............... 601/151 |
| 2008/0255494 A1 | 10/2008 | Rousso et al. |
| 2009/0018474 A1 | 1/2009 | Nakao |
| 2009/0118651 A1 | 5/2009 | Rousso et al. |
| 2010/0010404 A1 | 1/2010 | Nardi et al. |
| 2010/0010406 A1 | 1/2010 | Nardi et al. |
| 2010/0036299 A1 | 2/2010 | Gough |
| 2010/0204803 A1 | 8/2010 | Tozzi et al. |
| 2011/0009795 A1 | 1/2011 | Graham et al. |
| 2011/0066093 A1 | 3/2011 | Vess |
| 2011/0082401 A1 | 4/2011 | Iker et al. |
| 2011/0131839 A1 | 6/2011 | Ballin et al. |
| 2011/0196269 A1 | 8/2011 | Arkans |
| 2011/0245743 A1 | 10/2011 | Eddy |

FOREIGN PATENT DOCUMENTS

| | | |
|---|---|---|
| JP | H06 14722 Y2 | 4/1994 |
| JP | 1999-009633 | 6/1997 |
| JP | 2 669858 B2 | 10/1997 |
| JP | 2002-336320 | 5/2001 |
| JP | 2003-062023 | 8/2001 |
| WO | WO02/055005 | 7/2002 |
| WO | WO2004084790 | 10/2004 |
| WO | WO2004091463 | 10/2004 |
| WO | 2011/022305 A2 | 2/2011 |

OTHER PUBLICATIONS

International Search Report dated Apr. 17, 2007, in Europe, Patent Application No. PCT/GB2007/000244. 4 pages.

Written Opinion dated Jan. 24, 2007, in Europe, Patent Application No. PCT/GB2007/000244. 5 pages.

International Preliminary Report on Patentability dated Jul. 29, 2008, in Europe, Patent Application No. PCT/GB2007/000244. 6 pages.

* cited by examiner

CONTROL UNIT FOR A MEDICAL DEVICE

BACKGROUND OF THE INVENTION

This invention relates to a control unit assembly for use with a medical device and, particularly, a pneumatic medical device, such as a compression device for a limb. In particular, the invention relates to a control unit assembly for use with a mobile compression device suited for use in the treatment of venous leg ulcers, oedema, deep vein thrombosis and vascular disorders.

Various medical devices are known that require inflation of one or more cells with fluid to a desired pressure, for example, compression devices which are used to apply pressure or pressure offloading devices such as mattresses or cushions which are used to even out pressure points. Compression devices are known for applying compressive pressure to a patient's limb. These types of devices are used to assist mainly in the prevention of deep vein thrombosis (DVT), vascular disorders and the reduction of oedema. Prior art devices are adapted for use in a hospital setting in which they are used predominantly for the prevention of DVT in patients with a high risk for developing this condition. U.S. Pat. Nos. 5,117,812; 5,022,387; 5,263,473; 6,231,532; 6,440,093 and 6,463,934 disclose such devices.

Compression therapy is used in the treatment of venous leg ulcers. The treatment relies on the compression achieving a reduction in oedema and improved return of blood via the venous system. This in turn reduces the residence time for blood supplied to the lower limb and the severity of ischaemic episodes within the limb that can result in tissue breakdown.

Compression of the limb can be achieved by a pneumatic or hydraulic compression device.

WO 2004/084790 discloses one type of mobile compression device. By "mobile" it is meant that the user wearing the compression device has relative freedom to move about. The device of WO 2004/084790 comprises one or more fluid inflatable cuffs containing one or more cells arranged for fitting on to a leg or an arm. The device allows the adjustment of the pressure in the cells dependent on the pressure profile desired. The application of pressure by the cells in the sleeve or cuff is maintained by a pump and valves which are operated by an automatic control unit which detects the fall or rise in pressure in each cell throughout the device. Where excessive or deficient pressure is detected by a sensor located in the cell, the control unit activates the pump to restore the intended pressure.

In the compression devices of the prior art, the control unit is a separate component which is typically not integral to the compression device and remotely operated. This is often on the user's belt, placed in a pocket or carried around by hand which is inconvenient for the user.

As a control unit, generally, includes a pump, electronic circuitry, conduits for connecting the control unit to the compression device, valves, a source of power, etc., the control unit is usually quite large. Hence, the known control units are bulky and heavy. Therefore, positioning of the unit in the device has not been practical because attaching the known control units to an outer surface of the compression device would result in an excessive weight burden impairing the mobility of the user. Integral positioning is also unnecessary as most of the prior art devices are used in a hospital setting where mobility of the patient is not the main concern. Were the control unit to be positioned on the device, weight would be localized at the attachment point of the device resulting in a weight imbalance on the compression device.

Also, a bulky control unit protruding from an outer surface of the compression device permits the unit to be knocked and possibly broken when the user is mobile and would not fit beneath clothing.

There are barriers to reducing the size of the control unit. The conduits between the pump and the inflatable cells have in the past been external and would thus present a trip or tangle hazard. The power consumption by the components in a typical hospital device would make the battery too large to be carried on the device itself and would make it too bulky to fit under clothing.

The above disadvantages may contribute to low patient compliance and limit use. A control unit which is an integral part of a device with a low profile and whose internal components are miniaturized sufficiently so as not to affect the performance of the control unit or the medical device has therefore been sought.

SUMMARY OF THE INVENTION

According to a first aspect of the present invention, there is provided a control unit for a medical device wherein the control unit comprises a pump, a conduit and control means for controlling the flow of fluid from the pump through the conduit characterized in that the conduit is a rigid internal passage located in the control unit.

The control unit of the invention has the advantage that, as the conduits are rigid it is possible to make a detachable connection between the control unit and a docking unit which is part of the medical device. This also makes it possible for there to be no external conduits between the control unit and the docking unit on the medical device. In this way, the control unit can be readily attached and detached from the medical device.

According to a second aspect of the present invention, there is provided a control unit assembly for a medical device wherein the assembly comprises a control unit and a docking unit, the docking unit located on the medical device wherein
  a. the control unit comprises a pump, a conduit and control means for controlling the flow of fluid from the pump through the conduit; and
  b. the docking unit comprises a detachable fluid transfer connector which connects the conduit to an inflatable cell of the device.

Preferably, the docking unit also comprises a backing plate and the connector is a relatively inflexible connector of the plug and socket type. The connector, preferably, forms an air tight seal and allows the repeated attachment and removal of the control unit. The number and arrangement of the connectors will be adapted to suit the number of cells present in the device.

The provision of the backing plate with rigid connectors permits direct insertion of the control unit into the device and allows it to be removed and re-inserted. This overcomes the need for remote positioning of the control unit assembly. Instead, the pump draws air or fluid from an external source into the conduits and to the rigid fluid transfer connectors of the backing plate into the cells of the compression device.

The rigid connectors, where present, act to hold to the control unit assembly securely while permitting the control unit to be readily detached from the compression device. To assist in the securement of the control unit to the device, an additional press-fit retaining means which acts against a spring bias and can be released by the pressing of a button on the control unit may be provided.

The presence of the docking unit and the detachable fluid connectors gives the advantage that the control unit is removable and, therefore, reusable. This is because typically the control unit assembly is significantly more costly to produce. Designed as a separate unit, it can have a working life of many years and can be transferred between devices and between patients. For cost-effective treatment of patients, the recycling of the control unit, rather than its disposal after each patient, is desirable. In contrast, the medical device whose inner surfaces come into contact with the patient's skin are typically single use and disposed of once no longer required by a particular patient. In any case, compression devices will typically have a working life of no longer than six months. Hence, the easy removal of the control unit assembly from the medical device and replacement on another medical device is advantageous.

The invention further provides that the conduits in the control unit are preferably rigid internal passages wholly located within the control unit in the form of a manifold.

The term "manifold" means the fluid transfer conduits that form a labyrinth of passages in the rigid material of the control unit. Preferably, the conduits terminate in connectors suitable for making connections with other components of the control unit assembly and compression device. The manifold replaces the plurality of tubes between the pump and device and makes the control unit compact enough to be received in the docking unit. The docking unit is, preferably, a pouch within the outer contour of the device.

Preferably, the control unit further comprises a plurality of valves located between the pump and the conduits, the plurality of valves being arranged in a ranked or tiered hierarchical structure The term "hierarchical or ranked valve tree structure" means the that valves are arranged in ranks according to their proximity in the direction of fluid flow from the pump. The valve closest to the pump directs fluid flow to a further rank or ranks of valves. In this manner, the number of valves needed in the control unit to control the plurality of inflatable cells is reduced.

The provision of the ranked valve arrangement permits size reduction of the control unit by reducing the number of valves and, therefore, the space that they occupy and their power consumption. This permits the proximal positioning of the control unit assembly on or within an outer sleeve of a compression device. When placed discretely within an outer sleeve of the compression device, there are no external edges of the control unit which can be knocked or damaged during use resulting in improved patient safety, quality of patient life and control unit life. Furthermore, improved patient compliance is expected with such a discretely concealed unit.

The ranked valve tree structure of the valve assembly where present, advantageously provides a means of selectively varying the air or fluid pressure of individual cells in the compression device without simultaneously activating all of the valves. Furthermore, the ranked valve tree structure reduces the number of valves required to achieve pressure variation. The tree structure thus permits size reduction in the control unit as fewer valves are needed. Hence, this arrangement is particularly amenable to portable power sources such as a battery. The valves are preferably latching valves as they further reduce the power consumption in the device.

Further, according to the invention, a compression device for use on a limb comprising a control unit assembly according to the first and second aspects of the present invention is provided.

Preferably, the one or more detachable fluid transfer connectors of one aspect of the invention is adapted for connection with the air or fluid transfer conduits in the control unit and in the compression device. More preferably, this is achieved by a male connector tube on the control unit assembly being engageable with a female connector slot on the compression device or a female connector slot on the control unit assembly being engageable with a male connector tube on the compression device.

A latch can be used to retain the male and female parts in place in order to secure the control unit. Preferably, the latch can be easily released so that the control unit assembly can be removed from the compression device, for example, by pushing a button on the exterior of the compression device.

Any number of rigid air or fluid transfer connectors can be employed. However, preferably, four or five connectors will be present and this will be dependent on the requirements of the compression device. Preferably, the air or fluid transfer connectors are made of a rigid plastics material which can be integrally formed as part of the backing plate. This may be achieved, for example, by means of injection molding techniques during the manufacture of the docking unit or backing plate.

The control unit assembly of the first and second aspects of the invention may comprise an additional (booster) portable battery as a power source. This may be a re-chargeable nickel cadmium, nickel metal hydride or lithium ion battery or any other lightweight battery that provides sufficient power.

Preferably, the control unit is attached to the backing plate in a sliding press-fit to engage the connectors and the latch.

The compression device, preferably, has an outer surface with a pouch for receiving and holding the control unit assembly. The docking unit is positioned in the pouch and can conveniently be in the form of a backing plate.

The compression device may contain many inflatable cells dependent on the individual needs of a patient and may be adapted for an arm or a leg. In a preferred embodiment, the device is adapted for use below the knee of a patient and comprises three inflatable cells located in the region between the knee and the ankle and two inflatable cells located in the heel and foot region.

In another embodiment, the invention provides a control unit assembly for a medical device wherein the assembly comprises a control unit and a docking unit, the docking unit located on the medical device wherein the control unit comprises a pump, a conduit and control means for controlling the flow of air through the conduit and the docking unit comprises a detachable air inlet connector which provides air to the pump, the connector being provided with a filter.

In this way, the air inlet to the pump is provided with a filter on the device side of the assembly. Thus, when the device has reached the end of its useful life and is replaced, the control unit is indirectly provided with a new filter. If the filter were placed in the control unit, it would not be replaced during the lifetime of the control unit without servicing of the unit. In addition, the provision of the filter on the device side of the assembly means that contamination of the control unit and its electrical circuitry is limited. If the filter were present in the control unit, during operation of the device unfiltered air would be drawn into the control unit at least as far as the filter. As the filter is external to the control unit, only filtered air is drawn into the control unit. This gives the advantage that reliability of the control unit may be improved.

DETAILED DESCRIPTION OF THE INVENTION

Figure 1:
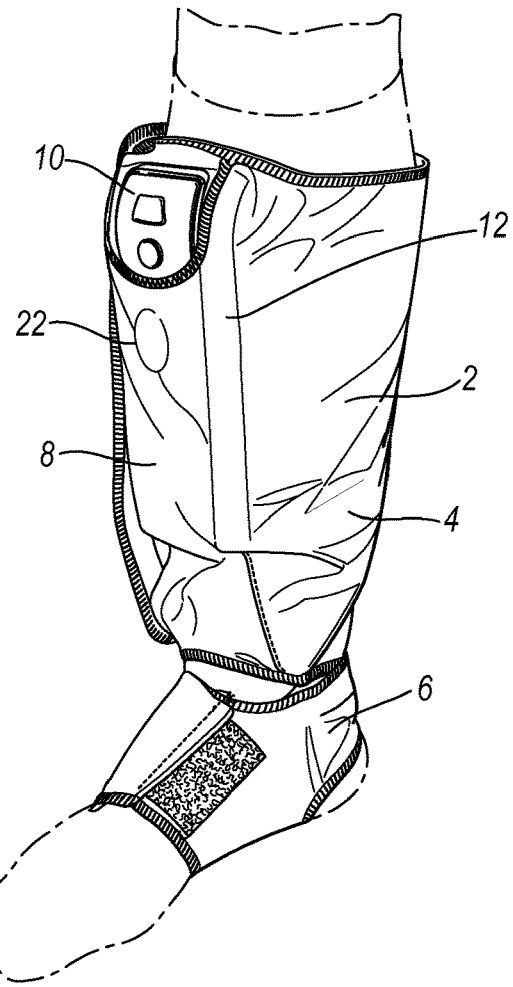
FIG. 1 is a perspective view of the control unit assembly of the invention integrated in a mobile compression device worn on the limb of a patient.

In FIG. 1 a control unit assembly and compression device according to an embodiment of the invention is shown worn on the leg of a patient. The device comprises a sleeve 2 having a leg cuff 4 connected to a foot cuff 6. The device also comprises a control unit assembly 8 comprising a control unit 10. The control unit 10 is small and when removed from the sleeve 2 may be hand held. The control unit 10 is battery powered and rechargeable so that it can be recharged when attached to or detached from the sleeve 2. FIG. 1 also shows the pouch 12 provided on sleeve 2 for receiving the control unit 10 and the low profile of the assembly. The control unit assembly follows the contour of the device and integrates the assembly into the device.

Figure 2:
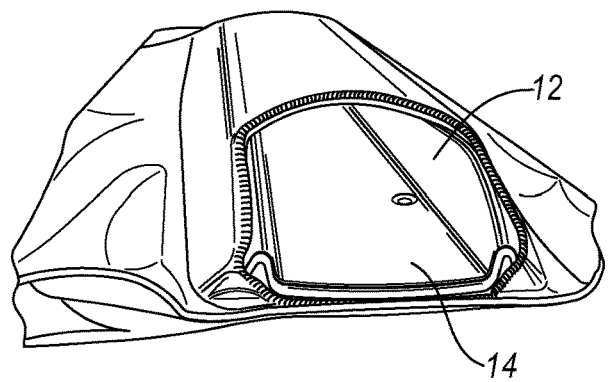
FIG. 2 is a perspective view of a backing plate for receiving a control unit to form the assembly of the invention.

FIG. 2 is a perspective view taken from above the device with the control unit 10 removed showing the interior of the pouch 12 and the backing plate 14. The control unit 10 may be slidably engaged in the pouch 12 and retained in position by a latching means. FIG. 1 shows a release button 22 positioned on the pouch 12 of the device which when depressed releases the control unit 10 from the pouch 12.

Figure 3:
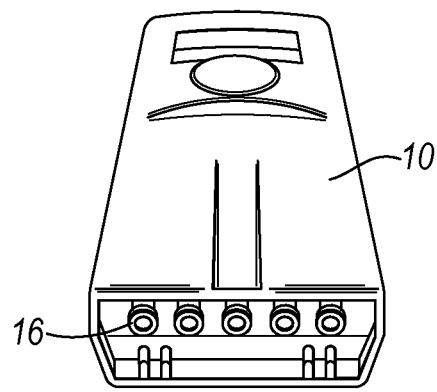
FIG. 3 is a perspective view of one end of the control unit of the invention showing the connectors which engage the connectors of the backing plate in use.

FIG. 3 is a perspective view of the control unit 10 removed from the pouch 12 and viewed from the bottom, showing the connectors 16 for engagement with the rigid connectors 18 of the backing plate 14.

Figure 4:
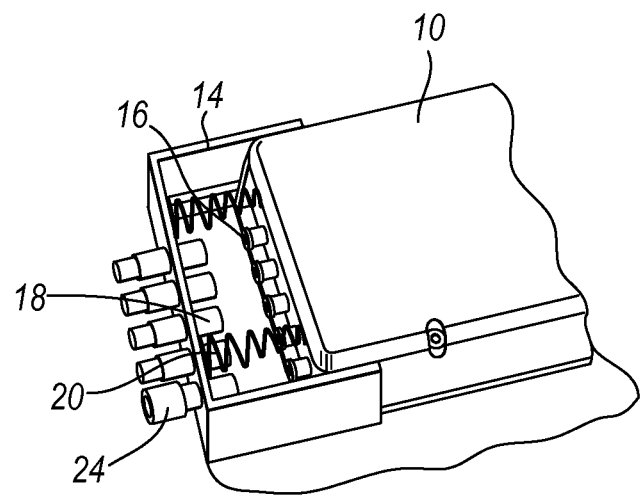
FIG. 4 is a perspective view of the backing plate and control unit of the assembly removed from the compression device to show the coming together of the connectors and the springs which bias the assembly apart for detachment of the control unit.

FIG. 4 is a perspective view of the backing plate 14, removed from the device for the purposes of illustration, showing the rigid connectors 18 for engagement with the connectors 16 of the control unit 10. FIG. 4 shows the control unit 10 being slid into engagement with the backing plate 14. As the control unit 10 is slid into the backing plate 14, it begins to compress two springs 20 which act to bias the control unit 10 and backing plate 14 apart. Further sliding movement of the control unit 10 causes the connectors 16, 18 to engage in a fluid tight seal and the control unit 10 to engage a latch (not shown) which retains the control unit 10 in the pouch 12 against the springs 20. The control unit 10 is released from the pouch 12 by depressing button 22 (FIG. 1), the outline of which is visible on the sleeve 2. The springs 20 then cause the control unit 10 and backing plate 14 to spring apart and the control unit 10 can be removed from the device. The springs 20 can be in the form of a leaf spring located in the backing plate 14 which similarly biases the parts of the assembly apart.

FIG. 4 also shows air filter 24 provided on the air inlet/outlet connector of the backing plate 14. As the air filter 24 is provided on the backing plate 14, it is naturally replaced when the control unit 10 is used with a new device. This reduces the service requirements of the control unit 10.

Figure 5:
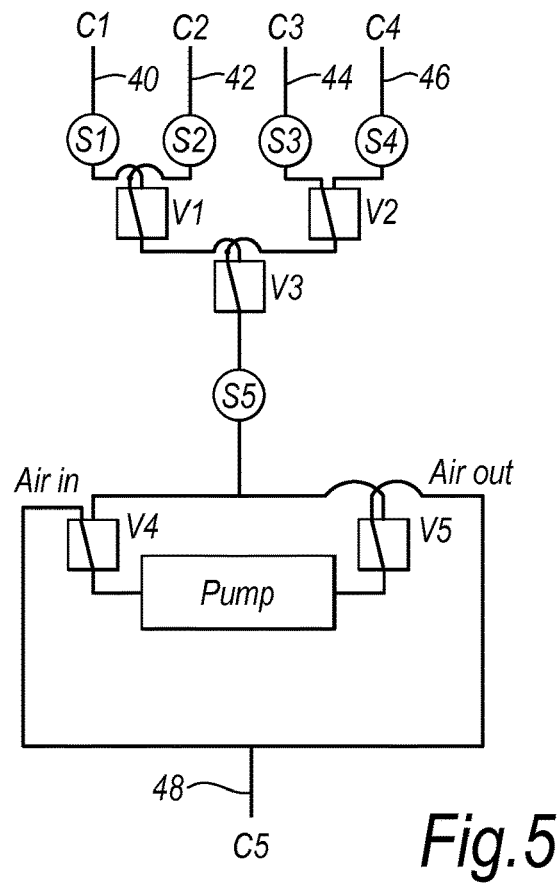
FIG. 5 is a schematic air flow logic diagram of the assembly of the invention.
Figure 6:
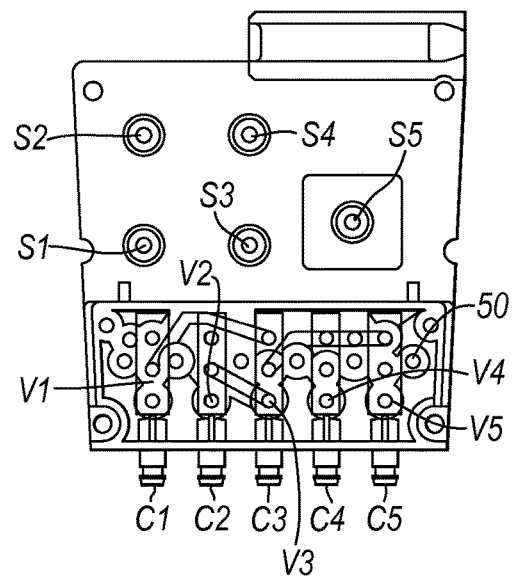
FIG. 6 is a schematic view of the interior of the control unit of the assembly of FIG. 1 showing the air manifold.

Referring to FIGS. 5 and 6, the control unit 10 has fluid flow conduits 40, 42, 44, 46, 48 which terminate in connectors C1, C2, C3, C4 and an air inlet/outlet C5. When a cell is required to be inflated, air is taken in via the conduit 48 by the operation of pump (labeled "PUMP") and valves V4 and V5 under instruction from a processor (not shown). The processor instructs valves V3, V1 and V2 which are arranged between the air inlet/outlet C5 and the conduits 40, 42, 44, 46 such that only one of the conduits 40, 42, 44, 46 is operational at any one time. From FIG. 5 it can be seen that valve V3 directs fluid from/to the air inlet/outlet C5 to/from either valve V1 or V2 which in turn selectively open or close fluid paths to connectors C1 or C2, or C3 or C4. The valves are preferably latching valves.

A sensor S1 (FIG. 6) is located in conduit 40 between connector C1 and valve V1 in the control unit 10. Similarly, sensors S2, S3 and S4 are located in conduits 42, 44, 46, respectively. Sensors S1 to S4 are all fluid pressure sensors controlled by a processor (not shown) and arranged to provide an indication of pressure exerted by the respective cells in the device. S5 independently monitors the pressure in the fluid flow system of the device.

FIG. 6 also shows the air manifold 50 with its labyrinth of passages that supplies air from the pump to each of the connectors C1 to C5. The air manifold 50 replaces the external tubes needed with prior art devices between a distal control unit and the connectors of the device.

We claim:

1. A control unit for a medical device, wherein the medical device comprises a compression device for a limb, wherein the compression device comprises a sleeve with one or more inflatable cells, wherein the compression device comprises a fluid transfer connector fixedly positioned on the sleeve of the compression device, the control unit configured to be received at a position on the sleeve of the compression device comprising:

a pump, a conduit, and control apparatus to control the flow of fluid from the pump through the conduit, wherein the conduit comprises a rigid internal passage located within the control unit which terminates in a connector configured to engage the fluid transfer connector fixedly positioned on the sleeve of the compression device as the control unit is being received on the sleeve of the compression device, wherein the fluid transfer connector that is fixedly positioned on the sleeve of the compression device comprises a rigid fluid transfer connector portion that is engaged by the connector which terminates the rigid internal passage of the control unit, the rigid fluid transfer connector portion that is engaged by the connector which terminates the rigid internal passage is in a fixed position on the sleeve of the compression device, wherein the entire rigid fluid transfer connector portion that is engaged by the connector which terminates the rigid internal passage is fixedly positioned on the sleeve of the compression device.

2. The control unit of claim 1, wherein the control unit comprises at least two conduits and at least one valve located between the pump and each conduit.

3. The control unit of claim 2, wherein the rigid internal passage forms an air manifold in the control unit.

4. The control unit of claim 3, wherein the control unit further comprises a plurality of valves located between the pump and the at least two conduits, the plurality of valves being arranged in a ranked valve structure.

5. The control unit of claim 4, wherein the ranked valve structure comprises a first rank latching valve connected to an external fluid source via the pump, which first rank latching valve when latched open in a first position, allows fluid to flow to a second rank latching valve which directs fluid flow between two conduits, said first rank latching valve, when latched open in a second position, allows fluid to flow to a further second rank latching valve which directs fluid flow between a further two conduits.

6. The control unit of claim 5, wherein each of the latching valves is located in the manifold of the control unit.

7. The control unit of claim 5, wherein the opening of a second rank latching valve in the ranked valve structure permits the transfer of fluid between a first inflatable cell and a second inflatable cell of the compression device.

8. The control unit of claim 5, wherein a pressure sensor is located between each conduit and the second rank latching valve which directs fluid thereto.

9. The control unit of claim 1, further comprising a portable battery as power source.

10. The control unit of claim 1, wherein the control apparatus comprises a processor.

11. A control unit assembly for a medical device, wherein the medical device comprises a compression device for a limb, wherein the compression device comprises a sleeve with one or more inflatable cells, the control unit assembly comprising:
a control unit; and
a docking unit, the docking unit located on the sleeve of the compression device, wherein the control unit comprises a pump, a conduit, and control apparatus to control the flow of fluid from the pump through the conduit, wherein the conduit comprises a rigid internal passage located within the control unit which terminates in one or more connectors and wherein the docking unit comprises one or more fluid transfer connectors which detachably connect to the one or more connectors of the control unit as the control unit is being received by the docking unit to connect the conduit of the control unit to at least one of the one or more inflatable cells of the compression device,
wherein the docking unit is fixedly positioned on the sleeve of the compression device, wherein each of one or more of the fluid transfer connectors of the docking unit comprises a rigid fluid transfer connector portion that is engaged by a connector which terminates the rigid internal passage of the control unit, the rigid fluid transfer connector portion that is engaged by the connector which terminates the rigid internal passage is in a fixed position on the sleeve of the compression device,
wherein the entire rigid fluid transfer connector portion that is engaged by the connector which terminates the rigid internal passage is fixedly positioned on the sleeve of the compression device.

12. The control unit assembly of claim 11, wherein the docking unit comprises a backing plate which carries the one or more fluid transfer connectors and the control unit slides into connection with the backing plate to form a fluid tight seal between the one or more fluid transfer connectors of the docking unit and the one or more connectors of the control unit.

13. The control unit assembly of claim 11, wherein the docking unit is located in a pouch on an outer surface of the sleeve, wherein the pouch is configured to receive the control unit.

14. The control unit assembly of claim 11, wherein the compression device is adapted for use below a knee of a patient and comprises inflatable cells located in a heel and foot region.

15. The control unit assembly of claim 11, wherein the compression device comprises at least two inflatable cells, each cell connected to a fluid transfer connector of the one or more fluid transfer connectors of the docking unit which in turn engages with a connector of the one or more connectors terminating the conduit in the control unit.

16. The control unit assembly of claim 11, wherein the conduit in the control unit terminates in the one or more connectors able to engage the one or more fluid transfer connectors of the docking unit to form a fluid tight seal.

17. The control unit assembly of claim 11, wherein the control unit, when assembled with the docking unit, is integrated into the outer contour of the compression device.

18. A control unit assembly for a medical device, wherein the medical device comprises a compression device for a limb, wherein the compression device comprises a sleeve with one or more inflatable cells, the control unit assembly comprising:
a control unit; and
a docking unit, the docking unit located on the sleeve of the compression device, wherein the control unit comprises a pump, at least one conduit, and control means for controlling the flow of air from the pump through the at least one conduit, wherein the at least one conduit comprises a rigid internal passage located within the control unit which terminates in a plurality of connectors; and wherein the docking unit comprises at least one fluid transfer connector which detachably connects to at least one connector of the plurality of connectors of the control unit as the control unit is being received by the docking unit to connect the at least one conduit of the control unit to an inflatable cell of the compression device and an air inlet connector which detachably connects to at least one connector of the plurality of connectors of the control unit and which provides air to the pump, the air inlet connector being provided with a filter,
wherein the docking unit is fixedly positioned on the sleeve of the compression device, wherein each of the at least one fluid transfer connectors of the docking unit comprises a rigid fluid transfer connector portion that is engaged by a connector of the plurality of connectors which terminates the rigid internal passage of the control unit, the rigid fluid transfer connector portion that is engaged by the connector which terminates the rigid internal passage is in a fixed position on the sleeve of the compression device,
wherein the entire rigid fluid transfer connector portion that is engaged by the connector which terminates the rigid internal passage is fixedly positioned on the sleeve of the compression device.

19. The control unit assembly of claim 18, wherein the docking unit comprises a plurality of fluid transfer connectors in addition to the air inlet connector detachably connectable to a plurality of conduits in the control unit.

20. The control unit assembly of claim 19, wherein the plurality of fluid transfer connectors connect the plurality of conduits to inflatable cells of the compression device.

\* \* \* \* \*